United States Patent [19]

Hopp et al.

[11] Patent Number: 5,319,104
[45] Date of Patent: Jun. 7, 1994

[54] DERIVATIVES OF CYCLIC LACTONES, A PROCESS FOR THEIR PREPARATION AND A PROCESS FOR THE PREPARATION OF 15-PENTADECANOLIDE AND ITS HOMOLOGUES

[75] Inventors: Rudolf Hopp; Horst Finkelmeier, both of Holzminden; Oskar Koch, Goettingen; Alfred Körber, Holzminden, all of Fed. Rep. of Germany

[73] Assignee: Haarmann & Reimer GmbH, Holzminden, Fed. Rep. of Germany

[21] Appl. No.: 875,867

[22] Filed: Apr. 29, 1992

[30] Foreign Application Priority Data

May 9, 1991 [DE] Fed. Rep. of Germany ....... 4115182

[51] Int. Cl.$^5$ .................... C07F 9/06; C07D 313/00
[52] U.S. Cl. .................................. 549/222; 549/271
[58] Field of Search ............................... 549/222, 271

[56] References Cited

U.S. PATENT DOCUMENTS 3,697,547 10/1972 Kurath et al. ............... 549/271
4,187,222 2/1980 Bauer et al. ................. 549/271

FOREIGN PATENT DOCUMENTS 1090182 4/1989 Japan .

*Primary Examiner*—C. Warren Ivy
*Assistant Examiner*—A. A. Owens
*Attorney, Agent, or Firm*—Sprung Horn Kramer & Woods

[57] ABSTRACT

The invention relates to new derivatives of macrocyclic lactones, a process for their preparation, a pyrolysis process using these new derivatives and the use of the pyrolysis products for the preparation of saturated macrocyclic lactones.

2 Claims, No Drawings

DERIVATIVES OF CYCLIC LACTONES, A PROCESS FOR THEIR PREPARATION AND A PROCESS FOR THE PREPARATION OF 15-PENTADECANOLIDE AND ITS HOMOLOGUES

The invention relates to new derivatives of cyclic lactones, which are suitable for the preparation of 15-pentadec-11/12-enolide and its homologues, starting substances for the preparation of 15-pentadecanolide (=15-hydroxy-pentadecanoic acid lactone) and its homologues, a process for the preparation of these new derivatives and a process for the preparation of 15-pentadecanolide and its homologues which starts from these new derivatives.

As is known, musk is rare and expensive. Fragrances having a musk-like smell which are more easily accessible are therefore sought-after components for the fragrance industry. 15-Pentadecanolide of the formula

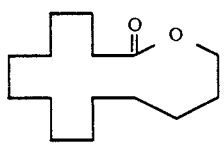

(I)

is a constituent of angelica root oil and—like its immediate homologues—has a delicate musk-like smell and the ability to act as a fixative. Intense effort has therefore already been made in the preparation of such macrocyclic lactones. Currently the most important syntheses start from 13-oxabicyclo[10.4.0]hexadec-1(12)-ene II, which can be prepared, for example, by free radical addition of allyl alcohol onto cyclododecanone and acid-catalysed dehydration of the resulting 2-(γ-hydroxypropyl)-cyclododecanone (German Auslegeschrift 2,136,496):

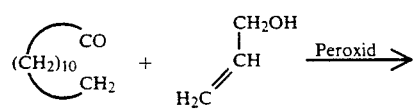

cyclododecanone

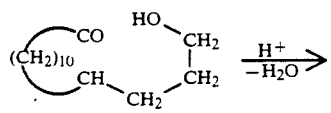

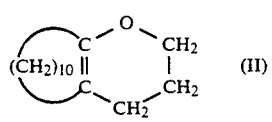

According to another process, hydrogen peroxide or alkyl peroxide is added onto II in the presence of sulphuric acid. Cleavage of the resulting 12-hydroperoxy-13-oxabicyclo[10.4.0]hexadecane (III) by heat or initiated by UV leads to 15-pentadecanolide (I) and to 15-pentadecenolides, which can be hydrogenated to give I (German Auslegeschrift 2,026,056):

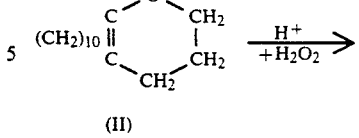

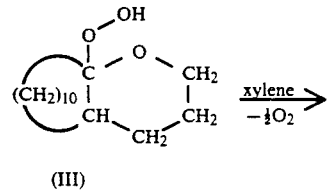

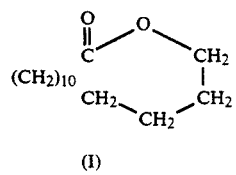

Another process utilises the 12-oximino-15-pentadecanolide (IV) accessible from II by nitrosation, the corresponding 12-ketone or the 12-hydrazone; reduction by the Wolff-Kishner or Huang-Minlon method gives 15-hydroxypentadecanoic acid (V)

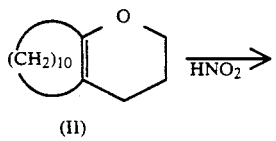

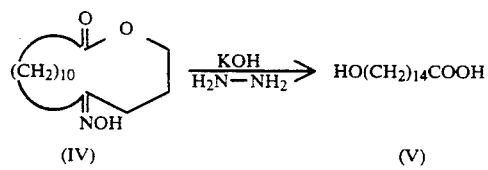

which can in turn be cyclised to give I, in which case it is preferably first subjected to condensation to give the polyester, which can be depolymerised to give I by vacuum distillation analogously to the method of W. H. Carothers, J. Amer. Chem. Soc. 58, 654 (1936) (German Offenlegungsschrift 2,731,543).

The process of Russian Inventor's Certificate 521,274 is a variant in which the macrocyclic ring is retained in all the reaction steps: II is converted into 12-oxo-15-pentadecanolide (VI) using butyl nitrite/sodium bisulphite, and the product is reduced by the Clemmensen method to give 15-pentadecanolide:

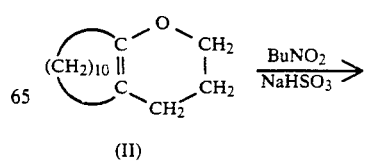

-continued

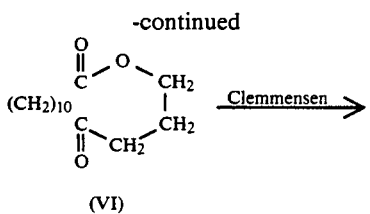

(VI)

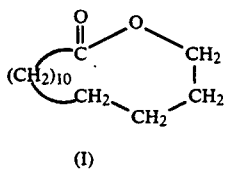

(I)

The yield of I in this process is only 36%, as can be seen from the examples. Electrochemical reduction of VI to I in accordance with German Offenlegungsschrift 3,127,242 also proceeds in only moderate yields of about 60%.

The preservation of the macrocyclic ring during the reduction operation is furthermore described in Brazilian Patent 81 08,358, the tosylhydrazone of VI being reduced to I by means of expensive borohydrides (for example Na cyanoborohydride).

According to Russian Inventor's Certificate 1,133,274, the 12-ketone VI is reduced to 12-hydroxy-15-pentadecanolide (VII) in the presence of Raney nickel, this product is then dehydrated to give the corresponding 15-pentadec-11- and -12-enolides (VIII), for example in the presence of phosphoric acid, and these products are hydrogenated in the presence of a nickel catalyst to give I:

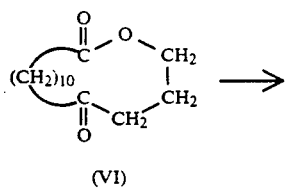

(VI)

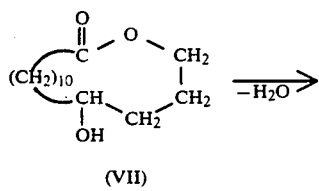

(VII)

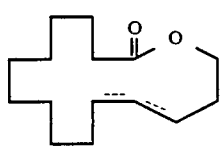

(VIII)

In our experience, the yields of 75 to 78% stated in the Inventor's Certificate are reduced to 50 to 60% for larger batches.

All the processes of the prior art discussed suffer from at least one deficiency which is considerable in terms of industrial production. Cyclisations are carried out in accordance with the dilution principle and therefore require disproportionately large amounts of solvent; during depolymerisation of polyesters, a high loss in yield results due to residue which cannot be worked up. Up until now, there was—in simple terms—the choice between easier processes with a poor yield and complicated processes with a better yield. An elegant process with a good yield was unknown to date.

Surprisingly, it has now been found that the hydroxylactones

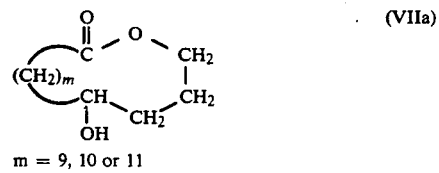

m = 9, 10 or 11 for example 12-hydroxy-15-pentadecanolide (m=10) can be reacted with suitable reagents to give corresponding derivatives IX, which can be pyrolysed exceptionally smoothly and in a high yield to give the unsaturated lactones

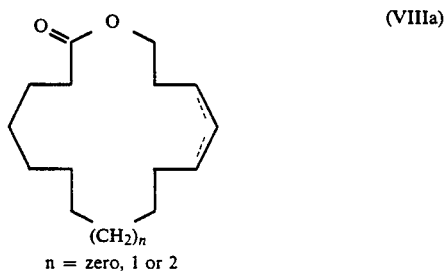

n = zero, 1 or 2 which can in turn be hydrogenated to give the saturated lactones

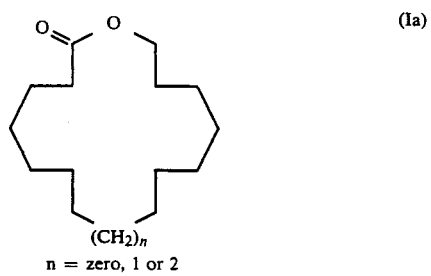

n = zero, 1 or 2

This is particularly unexpected inasmuch as according to the literature, for example J. Org. Chem. 42, 3895 (1977), under pyrolysis conditions macrocyclic lactones are split to give ω-alkenoic acids in high yields, the ring being opened. It has furthermore been found that this reaction can also be used on the corresponding homologues.

The invention thus relates to lactones of the formula

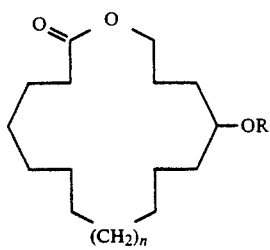 (IX)

wherein
n denotes zero, 1 or 2 and
OR is chosen from the series consisting of

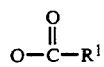 (1.)

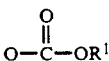 (2.)

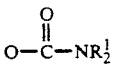 (3.)

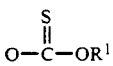 (4.)

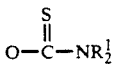 (5.)

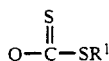 (6.)

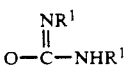 (7.)

wherein $R^1$ represents $C_1$-$C_{12}$-alkyl, preferably methyl, $C_6$-$C_{12}$-aryl, preferably phenyl or tolyl, or, in the case of (3.), phenylsulphonyl,

 (8.)

wherein
X = a free electron pair and Y = $R^1$, or
X = a free electron pair and Y = $OR^1$, or
X = a free electron pair and Y = Cl, or
X = O and Y = $R^1$, or
X = O and Y = $OR^1$, or
X = O and Y = Cl,
and $R^1$ denotes $C_1$-$C_4$-alkyl, phenyl or tolyl, and

 (9.)

wherein
X = $OR^1$ and Y = Cl, or
X = $OR^1$ and Y = $OR^1$, or
X = Cl and Y = Cl, and $R^1$ denotes $C_1$-$C_4$-alkyl, phenyl or tolyl.

The compounds (IX) according to the invention as intermediate products for the preparation of 15-pentadecanolide (I) and its homologues open up an elegant synthesis possibility, by which high yields can be achieved.

The invention furthermore relates to a process for the preparation of the compounds (IX), in which the hydroxylactone (VIIa) is reacted with a suitable, preferably commercially available reagent. Preferred such reagents include, for example (1.) carboxylic acid anhydrides or chlorides, preferably acetic anhydride, propionic anhydride, benzoyl chloride or pelargonyl chloride, (2.) chloroformic acid esters, preferably methyl chloroformate, (3.) alkyl and/or aryl isocyanates or alkyl- and/or arylsulphonyl isocyanates, preferably phenyl isocyanate and phenylsulphonyl isoyanate, (4.) chlorothioformic acid esters, preferably phenyl chlorothioformate, (5.) alkyl and/or aryl isothiocyanates, preferably phenyl isothiocyanate, (6.) carbon disulphide (and subsequent S-alkylation with) methyl iodide, (7.) dialkyl- and/or diarylcarbodiimides, preferably dicyclohexylcarbodiimide, (8.) sulphonic acid chlorides or alkylsulphonic acid chlorides, preferably methanesulphonyl chloride, (9.) phosphoric acid chlorides, preferably diethyl chlorophosphate.

The term "alkyl" in the sense of the present invention also includes "cycloalkyl".

The reaction is in general carried out using 0.9 to 2.0, preferably 1.0 to 1.5 mol of reagent per mol of hydroxylactone (VIIa) at temperatures from −5° C. to 150° C., preferably 0° C. to 135° C. Suitable catalysts can be employed in the customary manner.

The invention furthermore relates to a process for the preparation of the unsaturated lactones (VIIIa) by pyrolysis of the compounds IX.

The pyrolysis can be carried out at 110° C. to 450° C., preferably at 130° C. to 200° C.

The invention furthermore relates to a process for the preparation of saturated lactones (Ia) by conversion of the hydroxylactone (VIIa) into the compound IX, pyrolysis of IX to give VIIIa and subsequent hydrogenation.

The percentage data in the following examples relate to the weight.

EXAMPLES

A. Preparation of the starting substances

1. Preparation of 12-oxo-15-pentadecanolide (VI)

219 g (2.45 mol) of isopropyl nitrite, 880 g of isopropanol, 1,000 g of water and 79 g of 10% strength hydrochloric acid are initially introduced into a flask and cooled to 0° C. 500 g (2.16 mol) of decamethylenedihydropyran (II) (96% pure) are added dropwise to this mixture such that the internal temperature does not rise above 5° C. After the dropwise addition, the mixture is allowed to after-react at the same temperature for a further 2 hours. 600 g (5.8 mol) of sodium bisulphite are now admixed to the reaction mixture and the mixture is heated up to the reflux temperature. It is boiled under reflux for 2.5 hours. The organic phase is extracted in toluene, the extract is washed with bicarbonate and dried, the solvent is stripped off and the residue is subjected to fractional distillation. 480 g (1.89 mol) of 12-oxo-15-pentadecanolide are obtained;

boiling point: 145° C. under 0.5 torr, melting point: 33° C., yield 88% of theory.

2. Preparation of 12-hydroxy-15-pentadecanolide (VII) (method of reduction with NaBH₄)

A solution of 480 g (1.89 mol) of 12-oxo-15-pentadecanolide (VI) in 735 ml of methanol is cooled to 10°-15° C. 26.2 g of sodium borohydride are added in portions at this temperature. The mixture is allowed to after-react at 15° C. for a further 2 hours. After addition of water, excess methanol is distilled off. The organic content of the reaction mixture is extracted with toluene, the toluene phase is washed neutral and dried, the toluene is stripped off and the residue is subjected to fractional distillation. 470 g (1.85 mol) of 12-hydroxy-15-pentadecanolide are obtained;

boiling point: 165°-172° C. under 2 torr, melting point: 59°-61°C., yield 97% of theory.

3. Preparation of 12-hydroxy-15-pentadecanolide (VII) (method of hydrogenation)

480 g (1.89 mol) of 12-oxo-15-pentadecanolide (VI) are mixed with 1,000 g of isopropanol and hydrogenated in an autoclave with addition of 9.6 g of Raney cobalt under a hydrogen pressure of 100 bar at 135° C. After the solvent has been stripped off, distillation of the residue gives 460 g (1.80 mol) of 12-hydroxy-15-pentadecanolide.

Yield: 95% of theory.

B. Preparation of the derivatives IX

1. Preparation of 12-acetoxy-15-pentadecanolide

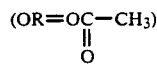

473 g (4.64 mol) of acetic anhydride are initially introduced into a flask and heated to 135°-140° C. (reflux). 982 g (3.83 mol) of 12-hydroxy-15-pentadecanolide (VII) are added dropwise. The mixture is allowed to after-react under reflux for a further hour. The excess acetic acid/acetic anhydride is then distilled off under a weak vacuum. 1120 g of 12-acetoxy-15-pentadecanolide are obtained;

yield: 98% of theory.

2. Preparation of 12-methoxycarbonyloxy-15-pentadecanolide

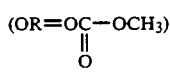

480 g (1.89 mol) of 12-hydroxy-15-pentadecanolide (VII) are dissolved in 900 ml of methylene chloride with 205.5 g of pyridine. 213 g (2.2 mol) of methyl chloroformate in 900 ml of methylene chloride are added dropwise to this mixture at 0° to 5° C. in the course of 1 hour. The reaction mixture is stirred at room temperature for a further 5 hours. The organic phase is washed neutral and dried over Na sulphate. The organic phase is freed from methylene chloride and subjected to fractional distillation. 540 g of 12-methoxycarbonyloxy-15-pentadecanolide are obtained; yield: 91% of theory.

3. Preparation of 12-N-phenylcarbamoyloxy-15-pentadecanolide

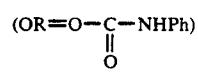

143 g (1.2 mol) of phenyl isocyanate are added to 256 g (1 mol) of VII in 600 ml of methylene chloride and the mixture is then heated under reflux for 3 hours. After the solvent has been removed, about 400 g of crude product are present; yield: 95% of theory.

4. Preparation of 12-phenoxythiocarbonyloxy-15-pentadecanolide

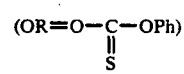

The preparation is carried out analogously to Example B2 using phenyl chlorothioformate;

yield: 89% of theory.

5. Preparation of 12-N-phenylthiocarbamoyloxy-15-pentadecanolide

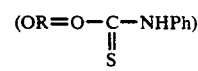

The preparation is carried out analogously to Example B3, using phenyl isothiocyanate;

yield: 90% of theory.

6. Preparation of 12-methylthio-thiocarbonyloxy-15-pentadecanolide

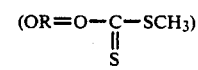

A total of 33 g (1.1 mol) of sodium hydride are added in portions to 256 g (1.0 mol) of VII in 1,000 ml of toluene at room temperature and the mixture is heated at 80° C. for 24 hours. After cooling, 84 g (1.1 mol) of carbon disulphide are added, the mixture is refluxed for 24 hours and cooled, 170 g (1.2 mol) of methyl iodide are then added and the mixture is refluxed again for 24 hours. After hydrolysis and washing several times with water, the solvent is stripped off, after which about 380 g of crude product are present;

yield: 90% of theory.

7. Preparation of 12-(N,N'-dicyclohexylamidinooxy)-15-pentadecanolide

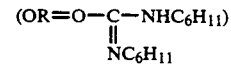

256 g (1.0 mol) of VII, 206 g (1.0 mol) of dicyclohexylcarbodiimide and 1 g of copper(I) chloride in 500 ml of ether are stirred at room temperature for 72 hours. After the solvent has been stripped off, about 460 g of crude product are present;

yield: 94% of theory.

8. Preparation of 12-mesyloxy-15-pentadecanolide

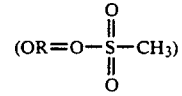

127 g of methanesulphonyl chloride are added to a solution of 256 g of VII in toluene in the presence of an equimolar amount of dimethylbenzylamine at a temperature of 30° C. and the mixture is stirred for 1 hour. After the organic phase has been washed and the solvent has been stripped off, the crude product is obtained;

yield: 95% of theory.

9. Preparation of 12-diethoxyphosphinyloxy-15-pentadecanolide $$(OR = O-P(OEt)_2)$$
     $\overset{\|}{O}$ A solution of 256 g (1.0 mol) of VII in 500 ml of ether is added dropwise to a suspension of 33 g (1.1 mol) of Na hydride in 300 ml of ether at 0° C. and the mixture is stirred at room temperature for 1 hour. 173 g (1.0 mol) of diethyl chlorophosphate in 200 ml of ether are then added at 0° C., after which the mixture is stirred at room temperature for a further 2 hours. After hydrolysis and stripping off the solvent, the crude product is obtained;

yield: 90% of theory.

C. Pyrolysis 1. (a) 1,120 g (3.75 mol) of 12-acetoxy-15-pentadecanolide from Example B1 are dripped through a pyrolysis tube which is heated at 430° C. and filled with glass packing. The pyrolysis product is extracted with toluene and the extract is washed with water and aqueous sodium bicarbonate solution. After distillation of toluene, a main fraction of 652 g is obtained at 110°–140° C./0.5 torr, which, according to the gas chromatogram, consists to the extent of 78% of a mixture of the 15-pentadecenolides; yield: 85% of theory.

(b) In the following example, the reaction temperature (splitting off of acetate) is lowered to 135°–180° C. by using the catalyst zinc chloride (otherwise analogously to 1a).

47 g of zinc chloride are added to 471 g (1.58 mol) of 12-acetoxypentadecanolide in a flask. Acetic acid is split off during heating at 135°–180° C. under a waterpump vacuum (20 torr) and is distilled off at an overhead temperature of 50°–60° C.

The reaction has ended when no further acetic acid is split off (3 to 5 hours). The residue which remains is extracted with toluene and the extract is washed neutral, dried and distilled under a high vacuum. 341 g are obtained, which consist to the extent of 96% of the isomeric 15-pentadecenolides; yield: 87% of theory.

2. The 12-methoxycarbonyloxy-15-pentadecanolide from Example B2 is reacted analogously to the pyrolysis according to Example C1a, the temperature being kept at 350°–400° C.; yield: 86% of theory.

3. The crude carbamate from Example B3 is heated at 200° C. for 3 hours and, after cooling, is taken up in toluene. After washing with water and removal of the solvent, the mixture of 15-pentadecenolides is distilled over; yield: 90% of theory.

4. The reaction of the derivative from Example B4 is carried out analogously to C2; yield: 80% of theory.

5. The pyrolysis of the thiocarbamate from Example B5 is carried out analogously to C3; yield: 85% of theory.

6. The crude xanthogenate from Example B6 is subjected to pyrolysis according to C3; yield: 80% of theory.

7. The crude product from Example B7 is heated at 200° C./5 mbar, the mixture of 15-pentadecenolides formed being distilled over continuously; yield: 80% of theory.

8. The mesyloxy derivative from Example B8 is heated at 160° C. in the presence of an equimolar amount of dimethylbenzylamine for 1 hour. After cooling to room temperature, washing with water and distillation, the 15-pentadecenolides are obtained; yield: 95% of theory.

9. The crude phosphate from Example B9 is treated analogously to the pyrolysis C8; yield: 90% of theory.

D. Hydrogenation 652 g of the product from Example C1 are mixed with 1,000 ml of methanol and 32.6 g of Raney nickel in an autoclave and hydrogenated with hydrogen under a pressure of 20 bar at 20° C. After working up, 488 g of pentadecanolide (I) are obtained by fractional distillation;

Boiling point: 110°–114° C./0.5 torr; yield: 95.3% of theory.

We claim:

1. Lactones of the formula (IX)

[Structure: macrocyclic lactone with $(CH_2)_n$ chain and OR substituent]

wherein
n denotes zero, 1 or 2 and
OR is chosen from the series consisting of $$O-\overset{\overset{O}{\|}}{C}-R^1 \quad (1.)$$

$$O-\overset{\overset{O}{\|}}{C}-OR^1 \quad (2.)$$

$$O-\overset{\overset{O}{\|}}{C}-N(R^1)_2 \quad (3.)$$

$$O-\overset{\overset{S}{\|}}{C}-OR^1 \quad (4.)$$

$$O-\overset{\overset{S}{\|}}{C}-N(R^1)_2 \quad (5.)$$

$$O-\overset{\overset{S}{\|}}{C}-SR^1 \quad (6.)$$

$$O-\overset{\overset{NR^1}{\|}}{C}-NHR^1 \quad (7.)$$

wherein $R^1$ represents $C_1$–$C_6$ alkyl, phenyl, tolyl or, in the case of (3.), phenylsulphonyl,

(8.)

wherein
X = a free electron pair and Y = $R^1$, or
X = a free electron pair and Y = $OR^1$, or
X = a free electron pair and Y = Cl, or
X = O and Y = $R^1$, or
X = O and Y = $OR^1$, or
X = O and Y = Cl,
and $R^1$ denotes $C_1$–$C_4$-alkyl, phenyl or tolyl, and

(9.)

wherein
X = $OR^1$ and Y = Cl, or
X = $OR^1$ and Y = $OR^1$, or
X = Cl and Y = Cl,
and $R^1$ denotes $C_1$–$C_4$-alkyl, phenyl or tolyl.

2. Lactones according to claim 1, wherein n denotes 1 and OR is chosen from the series comprising mesyl, tosyl and acetoxy.

* * * * *